United States Patent
Pazenok et al.

(10) Patent No.: US 9,630,898 B2
(45) Date of Patent: Apr. 25, 2017

(54) METHOD FOR PRODUCING HALOGENKETONES

(71) Applicant: BAYER CROPSCIENCE AKTIENGESELLSCHAFT, Monheim am Rhein (DE)

(72) Inventors: Sergii Pazenok, Solingen (DE); Christian Funke, Leichlingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/029,594

(22) PCT Filed: Oct. 20, 2014

(86) PCT No.: PCT/EP2014/072388
§ 371 (c)(1),
(2) Date: Apr. 14, 2016

(87) PCT Pub. No.: WO2015/059067
PCT Pub. Date: Apr. 30, 2015

(65) Prior Publication Data
US 2016/0272563 A1    Sep. 22, 2016

(30) Foreign Application Priority Data

Oct. 23, 2013 (EP) .................... 13189817

(51) Int. Cl.
*C07C 45/00* (2006.01)
*C07C 45/67* (2006.01)
*C07C 49/167* (2006.01)

(52) U.S. Cl.
CPC .......... *C07C 45/676* (2013.01); *C07C 49/167* (2013.01)

(58) Field of Classification Search
CPC ..................................................... C07C 45/676
USPC ................................................. 568/388, 394
See application file for complete search history.

(56) References Cited

U.S. PATENT DOCUMENTS 5,093,532 A * 3/1992 Baasner .................. C07C 45/40
568/407
5,481,029 A * 1/1996 Braun ..................... C07C 45/48
560/234

FOREIGN PATENT DOCUMENTS

| DE | 4313794 A1 | 11/1994 |
| EP | 0623575 A1 | 11/1994 |
| WO | 2009000044 A1 | 12/2008 |
| WO | 2009000442 A2 | 12/2008 |

OTHER PUBLICATIONS

Cardillo et al., "A New Diastereoselective Synthesis of anti-a-Alkyl a-Hydroxy â-Amino Acids." 1999, Europ. J. of Organic Chemistry; 155-161.
Burdon et al., "The Sodium-Promoted Claisen Ester Condensations of Ethyl Per Fluoroalkanecarboxylates." Tetrahedron, 1964, vol. 20, 2163-2166.
International Search Report dated Jan. 16, 2015, issued in PCT/EP2014/072388.

* cited by examiner

*Primary Examiner* — Sikarl Witherspoon
(74) *Attorney, Agent, or Firm* — McBee Moore Woodward Vanik IP LLC

(57) ABSTRACT

The present invention describes a novel method for producing haloketones.

6 Claims, No Drawings

METHOD FOR PRODUCING HALOGENKETONES

CROSS REFERENCE TO RELATED APPLICATIONS

This application is a §371 National Stage Application of PCT/EP2014/072388, filed 20 Oct. 2014 which claims priority to EP 13189817.3, filed 23 Oct. 2013.

BACKGROUND

Field of the Invention

The present invention relates to a novel method for producing haloketones.

Description of Related Art

On page 1, above paragraph 6, which states, "The problem described hereinabove was solved by a novel method for producing haloketones of formula." please insert the following heading,

SUMMARY

Haloketones, for example difluoroacetone and trifluoroacetone, are important intermediates in the production of biologically active compounds: WO 2009/000442.

Difluoroacetone or trifluoroacetone can be produced from difluoroacetate or trifluoroacetic acid and methylmagnesium bromide for example (Isr. Journal of Chemistry, 1999, 39, 155). However, the yield for difluoroacetone is just 47% and that for trifluoroacetone is 56%.

Di- and trifluoroacetone can also be produced by cleavage of trifluoroacetoacetate in the presence of twenty percent strength sulphuric acid (Tetrahedron, 1964, 20, 2163). The disadvantage of this reaction is that it is difficult to find a suitable material of construction which does not corrode and in which the reaction can be carried out. Here, it is not only the sulphuric acid that is the corrosion-causing component but also the liberated fluoride. This combination makes it impossible to use steel enamel, stainless steel and also Hastelloy tanks.

EP0623575 (B1) describes the synthesis of ketones by reaction of a carboxylic acid with a ketoester in the presence of a catalytic amount of an onium salt:

$$CF_3COOH + CF_3C(O)CH(COOEt) + CH_3SO_3H \rightarrow CF_3COCH_3 + 2CF_3COOEt$$

This method is uneconomical: a carboxylic acid such as $CF_3COOH$ is additionally required. In addition, an ester is formed which causes problems with purifying the product.

The problem addressed by the present invention in view of the prior art described hereinabove is that of providing a method which does not have the aforementioned disadvantages and consequently provides a route to haloketones in high yields.

The problem described hereinabove was solved by a novel method for producing haloketones of formula (I)

where $R^1$ is haloalkyl, characterized in that ketoesters of formula (II)

where $R^2$ is alkyl or benzyl and $R^1$ is as defined above, are cleaved in the presence of phosphoric acid.

Surprisingly, the haloketones of formula (I) are obtained under the conditions of the invention in good yields and with high purity without having strongly corrosive reaction conditions and the method according to the invention consequently overcomes the abovementioned disadvantages of the production methods described in the prior art.

DETAILED DESCRIPTION OF A PREFERRED EMBODIMENT

Preference is given to a process according to the invention in which the radicals of the compounds of formulas (I) and (II) are defined as follows:

$R^1$ is selected from $CF_3$, $CF_2H$, $CF_2Cl$;

$R^2$ is selected from methyl, ethyl, n-propyl, benzyl.

Particular preference is given to a process according to the invention in which the radicals of the compounds of formulas (I) and (II) are defined as follows:

$R^1$ is $CF_2H$;

$R^2$ is selected from methyl, ethyl.

GENERAL DEFINITIONS

Haloalkyl: straight-chain or branched alkyl groups having 1 to 6 and preferably 1 to 3 carbon atoms, wherein some or all of the hydrogen atoms in these groups may be replaced by halogen atoms as mentioned above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Alkyl groups are for the purposes of the present invention linear, branched or cyclic saturated hydrocarbon groups. The definition $C_1$-$C_{12}$-alkyl encompasses the widest range defined herein for an alkyl group. Specifically, this definition encompasses methyl, ethyl, n-propyl, isopropyl, n-butyl, isobutyl, sec-butyl and t-butyl, n-pentyl, n-hexyl, 1,3-dimethylbutyl, 3,3-dimethylbutyl, n-heptyl, n-nonyl, n-decyl, n-undecyl or n-dodecyl for example.

METHOD DESCRIPTION

Scheme 1:

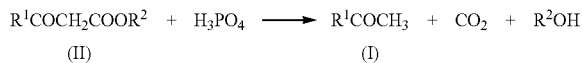

The ketoester compounds of formula (II) used as starting compounds are known and commercially available. The temperature during the reaction according to the invention is in the range of from 20° C. to 200° C., preferably in the range of from 70° C. to 130° C.

The method according to the invention can optionally be run as a continuous operation.

The quantity of $H_3PO_4$ is between 5 to 500 g for 1 mol of the compound of formula (I), preferably 20-350 g. Once the product has been isolated, the H3PO4 is reused without purification. At least 5 such cycles are possible without a drop in yield. It is preferable to use aqueous $H_3PO_4$ solution. The concentration of the $H_3PO_4$ is 20-85%, preferably 85%.

It is preferable to use technical-grade material having a content of 70-85%. It is also possible to use polyphosphoric acid. The reaction is optionally carried out in an inert solvent such as chlorobenzene, toluene. Corrosion of glass and metallic materials of construction was not observed for this method.

EXAMPLE 1

Difluoroacetone $HCF_2COCH_3$ 150 ml of $H_3PO_4$ (85% w/w) were initially charged to a 250 ml multi-necked flask equipped with a distillation bridge and heated to 100° C. to 105° C. 132 g of 91% w/w purity ethyl difluoroacetoacetate (0.720 mol) were added over 3 hours via a syringe pump. The distillate of boiling point 40-60° C. was continuously removed within 5 hours. The reaction is complete after 5 hours. A total of 75 g of clear colourless liquid were collected.

The composition of the fraction (determined by $^{19}F$ NMR) is:

70% w/w $HCF_2COCH_3$

11% w/w $HCF_2C(OH)_2CH_3$ hydrate

14% w/w $HCF_2C(OEt)(OH)CH_3$ monoketal

The mixture can be further used without purification. If desired, a second distillation over $H_3PO_4$ can be carried out for further purification. Hydrate and monoketal are simultaneously cleaved and converted to difluoroacetone.

Using 5 g of $H_3PO_4$ affords after distillation 67 g of difluoroacetone ($HCF_2COCH_3$) with a purity of 95% to 96%. The yield is 94% to 95%.

The invention claimed is:

1. Method for producing one or more haloketones of formula (I)

$$R^1COCH_3 \qquad (I),$$

where $R^1$ is haloalkyl, comprising cleaving one or more ketoesters of formula (II)

$$R^1COCH_2COOR^2 \qquad (II),$$

where $R^2$ is alkyl or benzyl and $R^1$ is as defined above, in the presence of phosphoric acid and without the addition of a carboxylic acid.

2. Method according to claim 1, wherein $R^1$ is selected from $CF_3$, $CF_2H$, or $CF_2Cl$; and $R^2$ is selected from methyl, ethyl, n-propyl, or benzyl.

3. Method according to claim 1, wherein $R^1$ is $CF_2H$; and $R^2$ is selected from methyl or ethyl.

4. Method according to claim 1, wherein said method is carried out at a temperature of from 70° C. to 130° C.

5. Method according to claim 1, wherein said method is carried out as a continuous operation.

6. A process for manufacturing a fungicidally active agent comprising the method according to claim 1.

* * * * *